(12) United States Patent
Propp

(10) Patent No.: US 8,049,057 B2
(45) Date of Patent: *Nov. 1, 2011

(54) REINFORCED CLOSURE ANCHOR

(75) Inventor: Donald J. Propp, Dewitt, MI (US)

(73) Assignee: Centurion Medical Products Corporation, Howell, MI (US)

(*) Notice: Subject to any disclaimer, the term of this patent is extended or adjusted under 35 U.S.C. 154(b) by 90 days.

This patent is subject to a terminal disclaimer.

(21) Appl. No.: 12/558,634

(22) Filed: Sep. 14, 2009

(65) Prior Publication Data

US 2010/0004680 A1 Jan. 7, 2010

Related U.S. Application Data

(63) Continuation of application No. 12/011,692, filed on Jan. 29, 2008, now Pat. No. 7,626,070.

(51) Int. Cl.
*A61C 13/00* (2006.01)
*A61D 1/00* (2006.01)
*A61M 5/32* (2006.01)

(52) U.S. Cl. .............................. 602/41; 606/213; 604/15

(58) Field of Classification Search .............. 602/41–43, 602/45, 52–54, 57–58; 606/213, 215, 139, 606/216, 228–232; 604/15, 180, 179, 174; 128/DIG. 26, 133, 132

See application file for complete search history.

(56) References Cited

U.S. PATENT DOCUMENTS

| 6,124,521 | A | 9/2000 | Roberts | |
|---|---|---|---|---|
| 7,025,749 | B2 * | 4/2006 | Propp | 604/180 |
| 7,294,752 | B1 * | 11/2007 | Propp | 602/58 |
| 7,626,070 | B2 * | 12/2009 | Propp | 602/41 |
| 7,723,561 | B2 * | 5/2010 | Propp | 602/58 |
| 2005/0131329 | A1 | 6/2005 | Beaudry | |
| 2005/0261623 | A1 | 11/2005 | Propp | |
| 2007/0060892 | A1 | 3/2007 | Propp | |
| 2008/0200880 | A1 | 8/2008 | Kyvik et al. | |
| 2010/0121282 | A1 * | 5/2010 | Propp | 604/180 |
| 2010/0160866 | A1 * | 6/2010 | Propp | 604/180 |
| 2010/0198162 | A1 * | 8/2010 | Propp | 604/180 |

* cited by examiner

*Primary Examiner* — Kim Lewis
*Assistant Examiner* — Tarla Patel
(74) *Attorney, Agent, or Firm* — Bill C. Panagos; Linda D. Kennedy; Rader, Fishman & Grauer PLLC

(57) ABSTRACT

A reinforced closure anchor includes a fabric layer having an adhesive side, an opposite non-adhesive side, and an outer edge. An anchor member layer having a reinforcing structure is disposed on the fabric layer. The anchor member is adhered to the fabric layer adhesive side. The anchor member is disposed within the outer edge of the fabric layer.

13 Claims, 5 Drawing Sheets

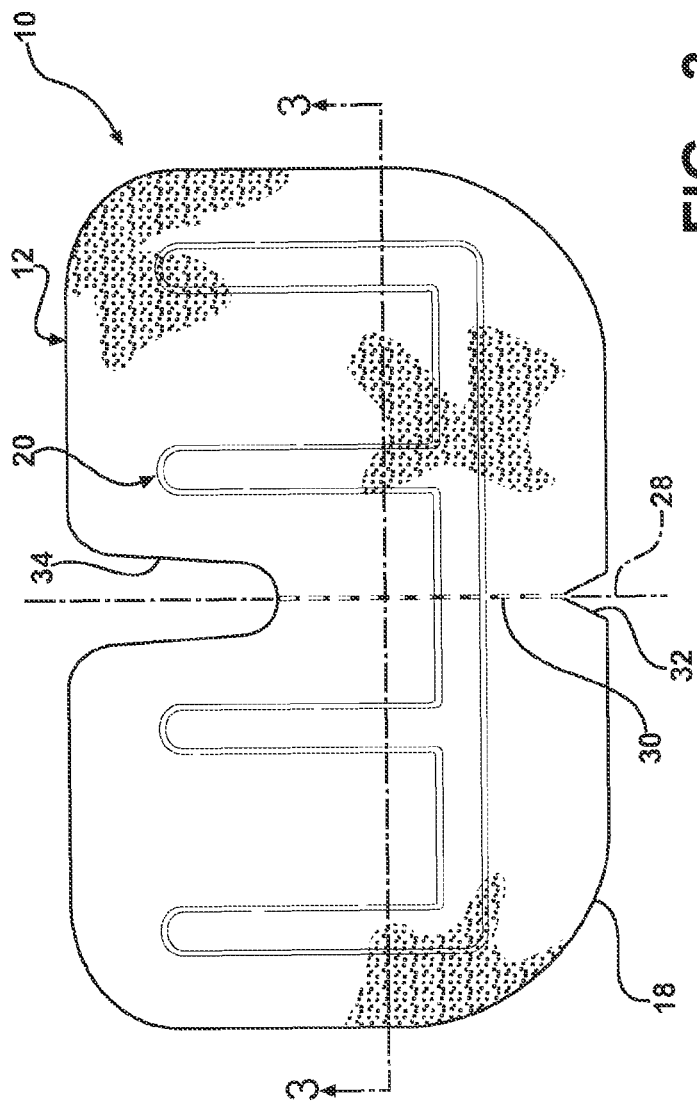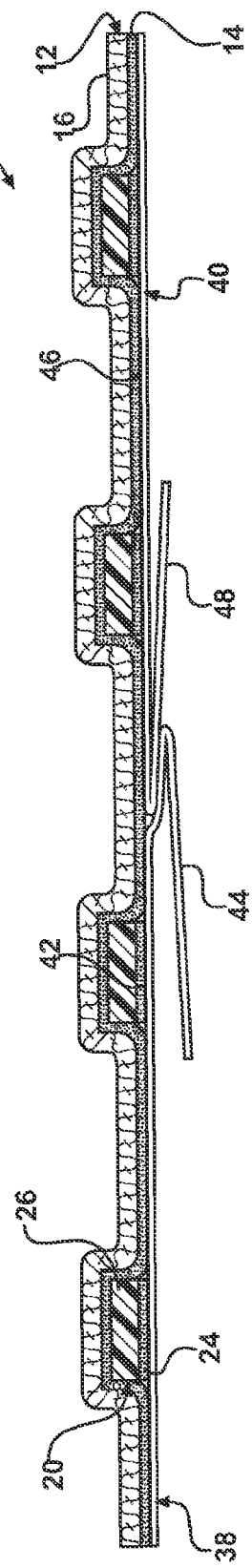

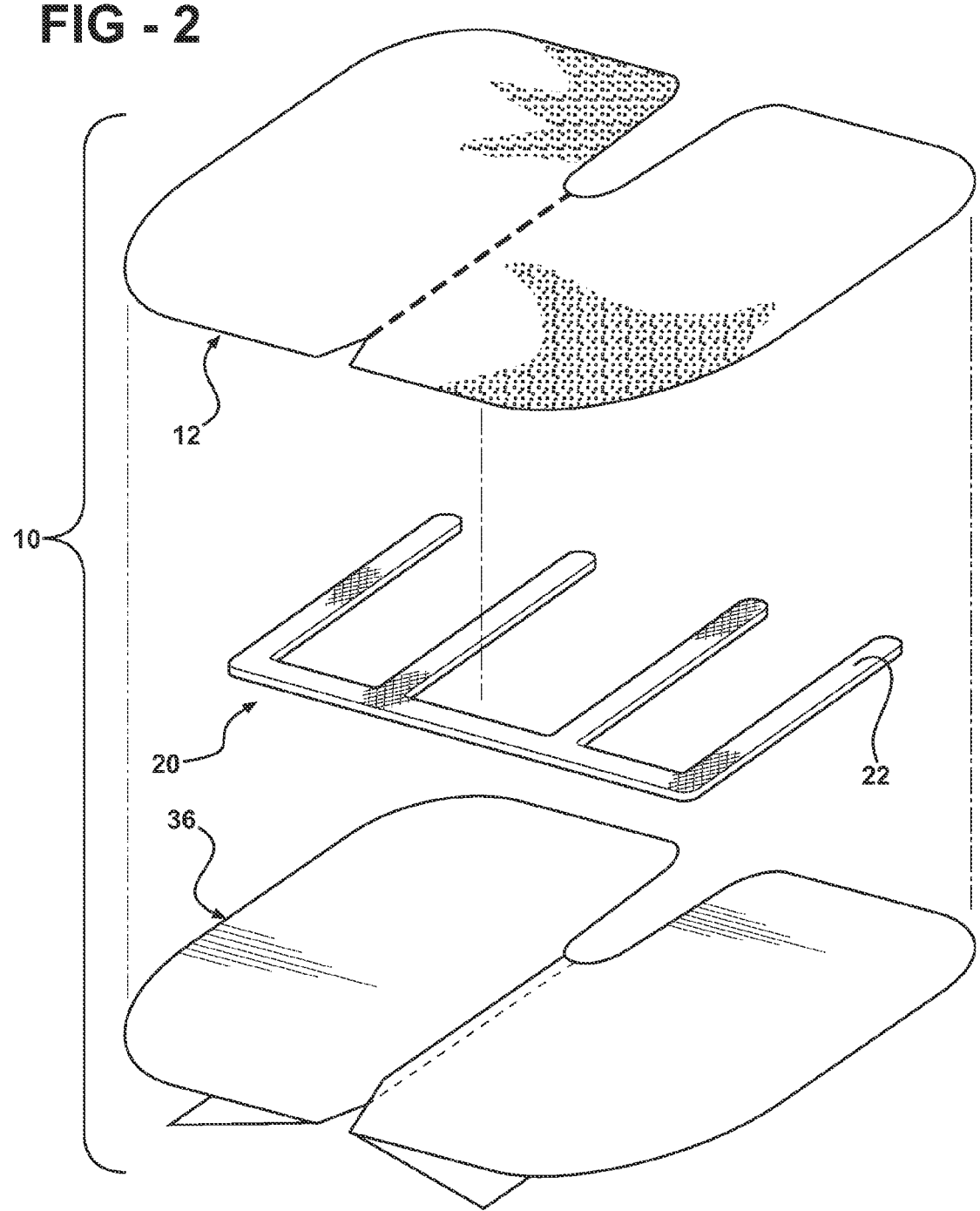

REINFORCED CLOSURE ANCHOR

CROSS REFERENCE TO RELATED APPLICATION

This application is a continuation of U.S. patent application Ser. No. 12/011,692, filed Jan. 29, 2008.

TECHNICAL FIELD

This invention relates to medical dressings, and more particularly to reinforced closure members for closing a portion of a medical dressing and anchoring medical tubing.

BACKGROUND OF THE INVENTION

It is known in the art relating to medical dressings for the protection and securement of catheters to apply a dressing to a patient's skin to cover a catheter insertion site at which the catheter punctures a patient's skin. It is also common for medical clinicians (i.e., doctors, nurses, and other medical personnel) to alternatively or additionally apply strips of medical grade tape to attempt to secure the catheter or associated medical tubing. Another conventional clinical practice is to suture a catheter hub to a patient's skin to roughly secure the catheter to the patient. Further still, a variety of catheter and medical tubing securement devices are available for use in the medical field. These securement devices, however, are often bulky and cumbersome, hard to dress with a dressing, and may have costly and complex mechanical features.

It is also known in the medical field that poorly dressed and poorly secured catheters and associated tubing are likely to undesirably lead to irritation of the insertion site, necessitating movement of the catheter to a new insertion site. Even worse, poorly secured catheters are susceptible to accidental dislodgement from the insertion site. For example, medical tubing connected to indwelling catheters, infusion needles and the like is often subjected to inadvertent but significant pulling forces either caused directly by patient movement or by snagging of the tubing on other objects. These pulling forces peel the medical tape or dressing securing the catheter and/or tubing off the patient's skin. This exposes the catheter, infusion needle, etc. to movement inward or outward, increasing the likelihood that the catheter, infusion needle, etc. will fail and have to be replaced and inserted into a new insertion site. Also, this may weaken the adhesion between the dressing and the patient's skin, potentially exposing the insertion site to harmful bacteria.

SUMMARY OF THE INVENTION

The present invention provides a reinforced closure anchor that can close over and anchor a slit, perforation, notch, or edge portion of a medical dressing at which a catheter and/or tubing exits from underneath the dressing. The reinforced closure anchor helps prevent a dressing from inadvertently peeling from a patient's skin, which may be caused by tugging on tubing that is under and exiting from the dressing, by both covering over a portion of the medical dressing and by securing an area of the dressing at which medical tubing exits from underneath the dressing. The reinforced closure anchor also prevents inadvertent peeling by providing additional material beyond the dressing edge, thereby greatly multiplying the dressing withstand in tug force vector directions opposite that which tubing exits from the dressing. Also, the reinforced closure anchor limits the amount of fabric cloth stretching that can occur by using relatively non-elastic reinforcement material for a spinal structure, which limits the amount and size of a "hole" that can be stretched open by tugs, and thus prevents catheter hubs and/or tubing from "oozing" out of a dressing.

More particularly, a reinforced closure anchor in accordance with the invention includes a fabric layer having an adhesive side, an opposite non-adhesive side, and an outer edge. An anchor member layer having a reinforcing structure, an adhesive side, and an opposite non-adhesive side is disposed on the fabric layer. The anchor member non-adhesive side is adhered to the fabric layer adhesive side. The anchor member may be disposed within the outer edge of the fabric layer, although it is within the scope of the invention for the anchor member to be coincident with the outer edge.

In one embodiment, the anchor member may be smaller in surface area than the fabric layer. For example, the anchor member may have less than half the surface area of the fabric layer. Also, the anchor member may cover only a portion of the fabric layer adhesive side. The anchor member may be a narrow fingers or spinal rib shape to ensure contourability to patient body curvatures, and to minimally reduce the breathability of the closure anchor, and of the dressing stack and closure anchor stack combination. The anchor member may be more or less than four tines and/or may be wider or narrowly spaced between the tines. Also, the anchor member may be very narrowly spaced between innermost tines, to create a "keyhole"-like effect at the dressing exit and the anchor member's innermost bottom of the U-shape, from which it is very difficult for a catheter hub to ever slide out of when the closure anchor is cinched up tightly to exiting tubing.

The reinforced closure anchor may also include a film layer having an adhesive skin adhering side. The film layer is adhered to the adhesive side of the anchor member and the fabric layer generally at the bottom of the closure anchor. The film layer may be a polyurethane film or similar and may have a shape that is coincident with the fabric layer. The film layer may make the closure anchor more comfortable for a patient by shielding the anchor member from the patient's skin, such as in a case where the anchor member is prickly. The film layer also can create a bacterial barrier and can add stack strength to the closure anchor.

The reinforced closure anchor may be generally symmetrical about one of its axes. A perforation line may extend across the fabric layer and the anchor member. The perforation line may extend along the axis of symmetry. A V-shaped notch may be disposed along the outer edge of the fabric layer at an end of the perforation line. A U-shaped indentation also may be disposed along the outer edge of the fabric layer.

The reinforced closure anchor may include a release liner releasably mounted on the adhesive side of the fabric layer. The release liner may include a first member and a second member. Each of the first member and second member may include a first portion mounted on the adhesive side of the fabric layer and a second portion folded relative to the first portion to form a gripping tab. One of the first and second members may overlap the other of the first and second members, and one of the first and second members may be released from the adhesive side of the fabric layer without tampering with the other of the members.

These and other features and advantages of the invention will be more fully understood from the following detailed description of the invention taken together with the accompanying drawings.

BRIEF DESCRIPTION OF THE DRAWINGS

In the drawings:

FIG. 1 is a plan view of one embodiment of a reinforced closure anchor in accordance with the invention;

FIG. 2 is an exploded view of the reinforced closure anchor of FIG. 1;

FIG. 3 is a cross-sectional view of the reinforced closure anchor taken along the line 3-3 in FIG. 1;

DETAILED DESCRIPTION OF THE INVENTION

Figure 4:
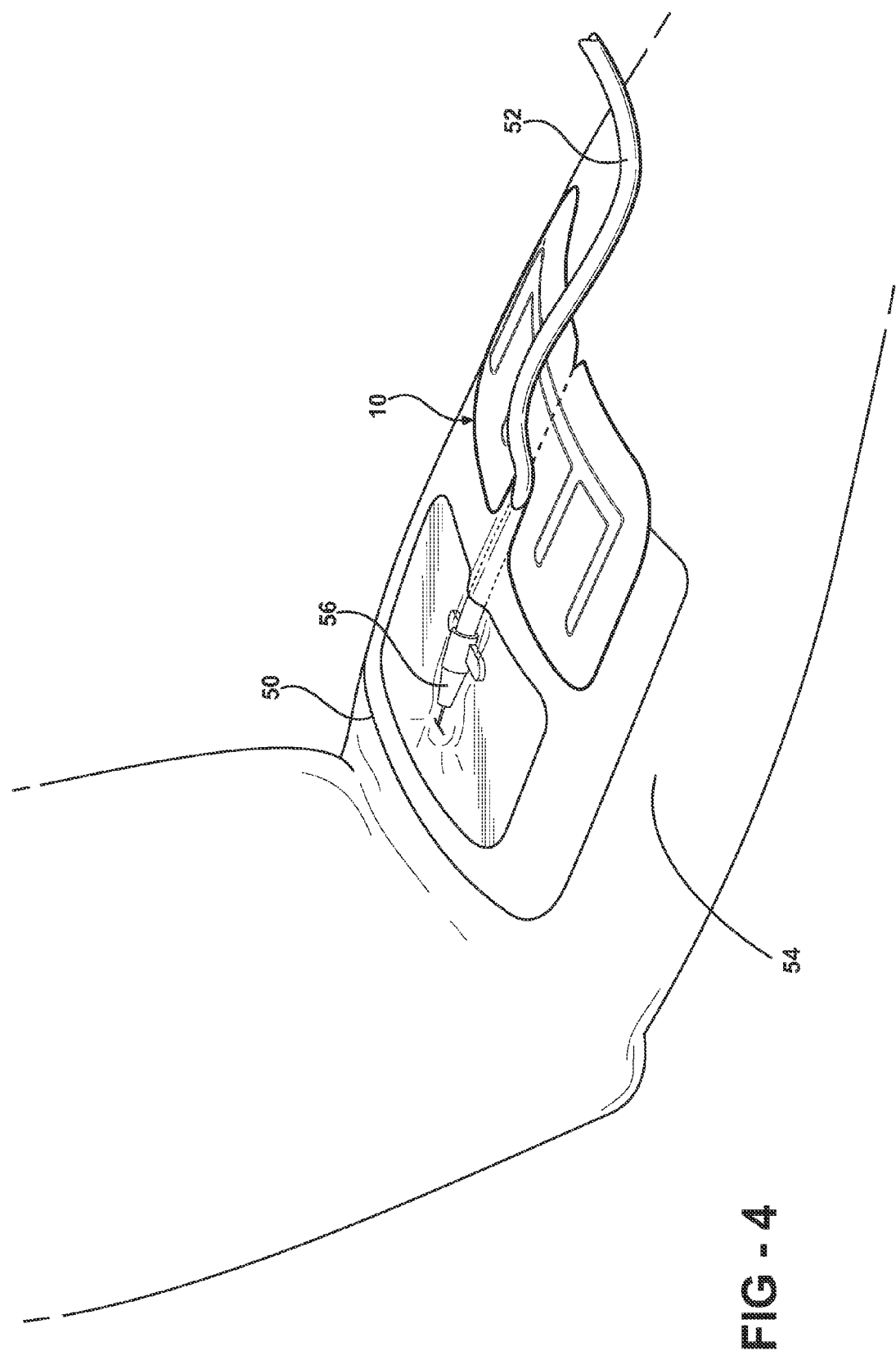
FIG. 4 is an environmental view of the reinforced closure anchor securing and stabilizing a dressing.

Referring now to the drawings in detail, numeral 10 generally indicates a reinforced closure anchor in accordance with the invention. The reinforced closure anchor 10 may secure a portion of a medical dressing, such as a portion at which medical tubing exits from underneath the dressing. The reinforced closure anchor 10 counteracts tugging forces from any hemispherical vector direction that may be applied on the medical tubing and helps prevent the tugging forces from pulling the dressing away from a patient's skin.

Turning to FIGS. 1 through 3, the reinforced closure anchor 10 includes a fabric layer 12 having an adhesive side 14 including a medical skin contact grade adhesive or similarly suitable adhesive thereon. The fabric layer 12 also has an opposite non-adhesive side 16 and an outer edge 18. The fabric layer 12 may be a woven or non-woven material. The fabric layer 12 is not limited to any particular shape. In the embodiment shown in the drawings, the fabric layer 12 is generally rectangular in shape with curved corners.

An anchor member layer 20 including a reinforcing structure 22 is disposed on the fabric layer 12. The anchor member 20 may be made of a polypropylene net material or another similar material, such as woven or non-woven materials having sufficient non-elastic properties yet being flexible, "contourable" and permeable, and having rigidizing and force spreading properties as discussed below, wherein the netting defines the reinforcing structure 22. The anchor member 20 has an adhesive side 24 including a medical skin contact grade adhesive or similarly suitable adhesive thereon. The anchor member 20 also has an opposite non-adhesive side 26. The anchor member non-adhesive side 26 is adhered to the fabric layer adhesive side 14. The anchor member 20 is disposed within the outer edge 18 of the fabric layer 12.

Figure 6:
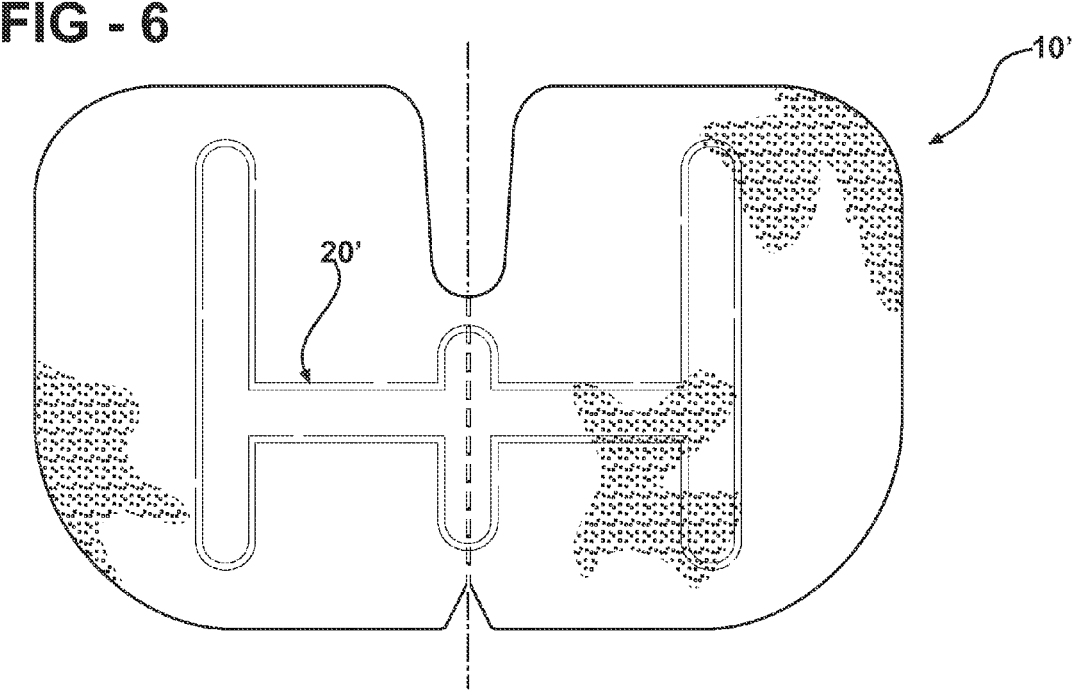
FIG. 6 is a plan view of a reinforced closure anchor in accordance with the invention.
Figure 7:
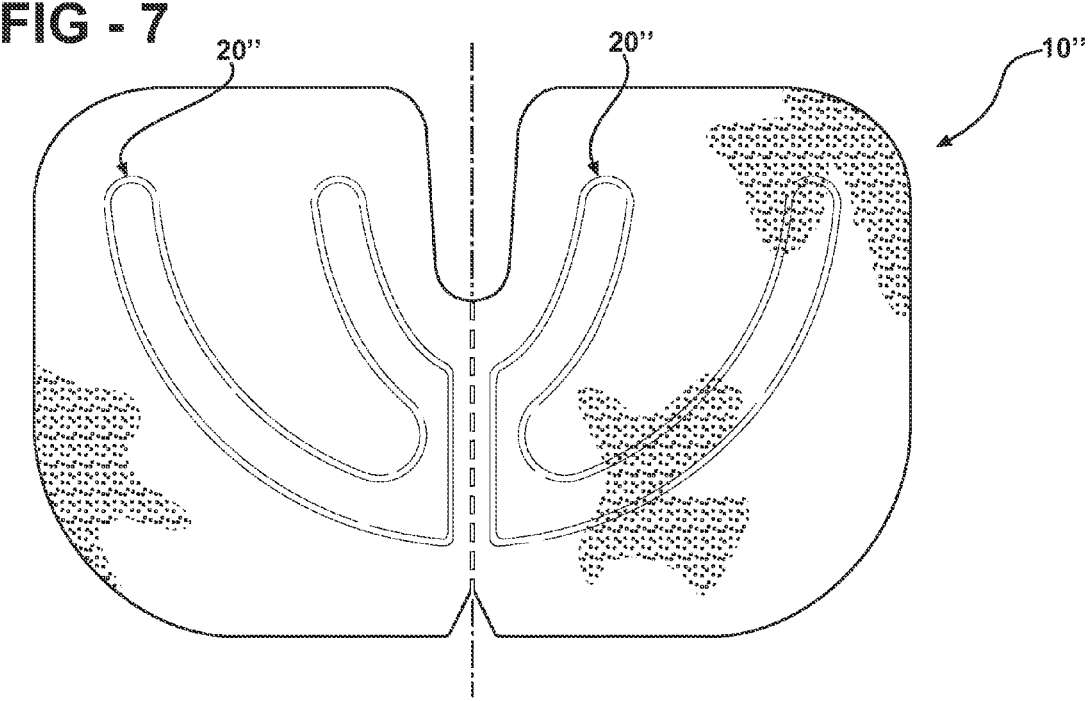
FIG. 7 is a plan view of a reinforced closure anchor in accordance with the invention.

The anchor member 20 is not limited to any particular shape, although the anchor member typically has less surface area than the fabric layer such that the anchor member only overlaps a portion of the fabric layer. For example, the anchor member 20 may have less than half the surface area of the fabric layer 12. In a first embodiment 10 and second embodiment 10' shown in FIGS. 1 and 6 respectively, the anchor member 20, 20' generally has a spinal rib shape that fits around and behind exiting catheter lumen, hubs, or IV tubing. In a third embodiment 10" shown in FIG. 7, the anchor member 20" has a narrow fingers shape to ensure contourability to patient body curvatures, and to minimally reduce the breathability of the closure anchor, and of the dressing stack and closure anchor stack combination. The anchor member may be more or less than four tines and/or may be wider or narrowly spaced between the tines. Also, the anchor member may be very narrowly spaced between innermost tines, to create a "keyhole"-like effect at the dressing exit and the anchor member's innermost bottom of the U-shape, from which it is very difficult for a catheter hub to ever slide out of when the closure anchor is cinched up tightly to exiting tubing.

The anchor member 20 strengthens the reinforced closure anchor 10 by making it less floppy for easier application. More importantly, as shown in FIG. 4, when the reinforced closure anchor 10 is applied over a portion of a dressing 50 and under the exiting tubing 52 (as well as to a patient's skin 54 where it is not over the dressing), the anchor member 20 spreads the localized external tubing tug forces that are exerted on the dressing 50 and the reinforced closure anchor 10 over a large surface area, greatly increasing the dressing's resistance to premature separation from the patient's skin by not permitting the dressing to elongate and break the adhesive forces between the dressing and the patient's skin. Likewise, the anchor member 20 increases the amount of force necessary to separate the dressing 50, and thus the catheter 56, from a patient's skin 54. With the use of the reinforced closure anchor 10, external forces exerted on a dressing are not as localized. Localized forces are a typical reason small forces are able to commence peeling of a dressing by stretching the fabric and film of the dressing in a local area which then propagates onward. Commonly, external forces are exerted on a dressing by pulling, snagging, or tugging on the ports, pigtails, fittings, and/or medical tubing that are connected to a catheter underneath the dressing. For example, movement of the medical tubing may be caused by the patient moving, by snagging of the tubing on other neighboring objects, by a clinician moving the tubing or the patient, or any combination of the above. The reinforced closure anchor 10 also prevents premature separation of a dressing from a patient's skin by preventing the dressing from stretching when the dressing is tugged on as described above, for example, when the tubing connected to the catheter hub is pulled. Stretching of a dressing locally can ultimately lead to a dressing separating fully from a patient's skin. In sum, the reinforced closure anchor 10 increases the withstand of a dressing and greatly increases the amount of any hemispherical vector multi-directional pulling force that is necessary to cause a dressing to separate from a patient's skin.

The reinforced closure anchor 10 may be generally symmetrical about one of its axes 28. A closure perforation line 30, for easy removal of the closure anchor and associated dressing, may extend across the fabric layer 12 and the anchor member 20. In other words, the reinforced closure anchor 10 is perforated through all of layers (not including any release liner layer(s)—see below) along the perforation line 30. The perforation line 30 may extend along the axis of symmetry 28, thereby dividing the reinforced closure anchor 10 into two mirror image portions and allowing the reinforced closure anchor to be separated at a dressing removal time while the closure anchor is still overlapped onto the dressing on either side of the tubing. A V-shaped notch 32 may be disposed along the fabric layer outer edge 18 at an end of the perforation line 30. The V-shaped notch 32 serves as a landmark indicating where the perforation line 30 is located. A deep U-shaped recess 34 is disposed along the fabric layer outer edge 18. The U-shaped recess 34 may be at an opposite end of the perforation line 30 relative to the V-shaped notch 32. When the reinforced closure member 10 is applied to a dressing in an area where medical tubing exits from underneath the dressing, closure anchor's U-shaped recess 34 is slid under the tubing and overlapped on top of the dressing behind the catheter hub, creating opposing U-slot "keyholes" that the catheter hub cannot be tugged out of. The U-slot "keyholes" and the added surface area beyond the dressing's edge strengthen the dressing and greatly increase the magnitude of a tug force necessary to raise the dressing's edge from a patient's skin, thereby improving securement and stabilization. The U-shaped recess 34 also makes it easier to create an occlusive barrier at the tubing exit point.

The reinforced closure anchor may further include a release liner 36 releasably mounted on the adhesive side 14 of the fabric layer 12. The release liner 36 may include a first member 38 and a second member 40. The first member 38 includes a first portion 42 and a second portion 44 and the second member 40 includes a first portion 46 and a second portion 48. The first portions 42, 46 are mounted on the fabric layer adhesive side 14 and the second portions 44, 48 are folded relative to the first portions to form gripping tabs. The first member 38 may overlap the second member 40, and each of the first and second members may be released from the fabric layer adhesive side 14 without tampering with the other of the members.

To apply the reinforced closure anchor 10, preferably only one of the first and second members 38, 40 of the release liner 36 is removed to expose part of the fabric layer adhesive side 14. For example, the first member 38 may be removed by gripping the gripping tab 44 and pulling the first member 38 away from the fabric layer adhesive side 14. By leaving the second member 40 of the release liner 36 in place, a user may grasp part of the reinforced closure anchor 10 without the user's fingers becoming stuck to the reinforced closure anchor. Next, the reinforced closure anchor 10 is positioned where it is desired to apply the reinforced closure anchor 10. For example, the reinforced closure anchor 10 may be applied to an edge portion of a dressing at which tubing exits from underneath the dressing. The reinforced closure anchor 10 is positioned so that the closure anchor is under the tubing with the U-shaped recess 34 laying one either side of the tubing and overlapping the top surface of the dressing. The exposed fabric layer adhesive side 14 is then adhered to the outside of the dressing and any portion of the patient's skin that is exposed underneath the reinforced closure anchor. Next, the second member 40 of the release liner 36 is removed by pulling the gripping tab 48, and the rest of the reinforced closure anchor 10 is applied to the dressing and/or patient's skin.

Alternatively, the reinforced closure anchor 10 may be used in lieu of tape strips to secure medical tubing, such as IV tubing, to a patient's skin.

To remove the closure anchor 10 and dressing from a patient's skin, the closure anchor is separated along the perforation line 30 by tearing the perforation line. The closure anchor 10 and dressing may then be removed from the patient's skin as a single unit by pulling the closure anchor 10 and dressing away from the tubing and catheter hub, making it safer and easier to remove the dressing from the tubing and hub with a lowered risk of unwanted catheter movement.

Figure 5:
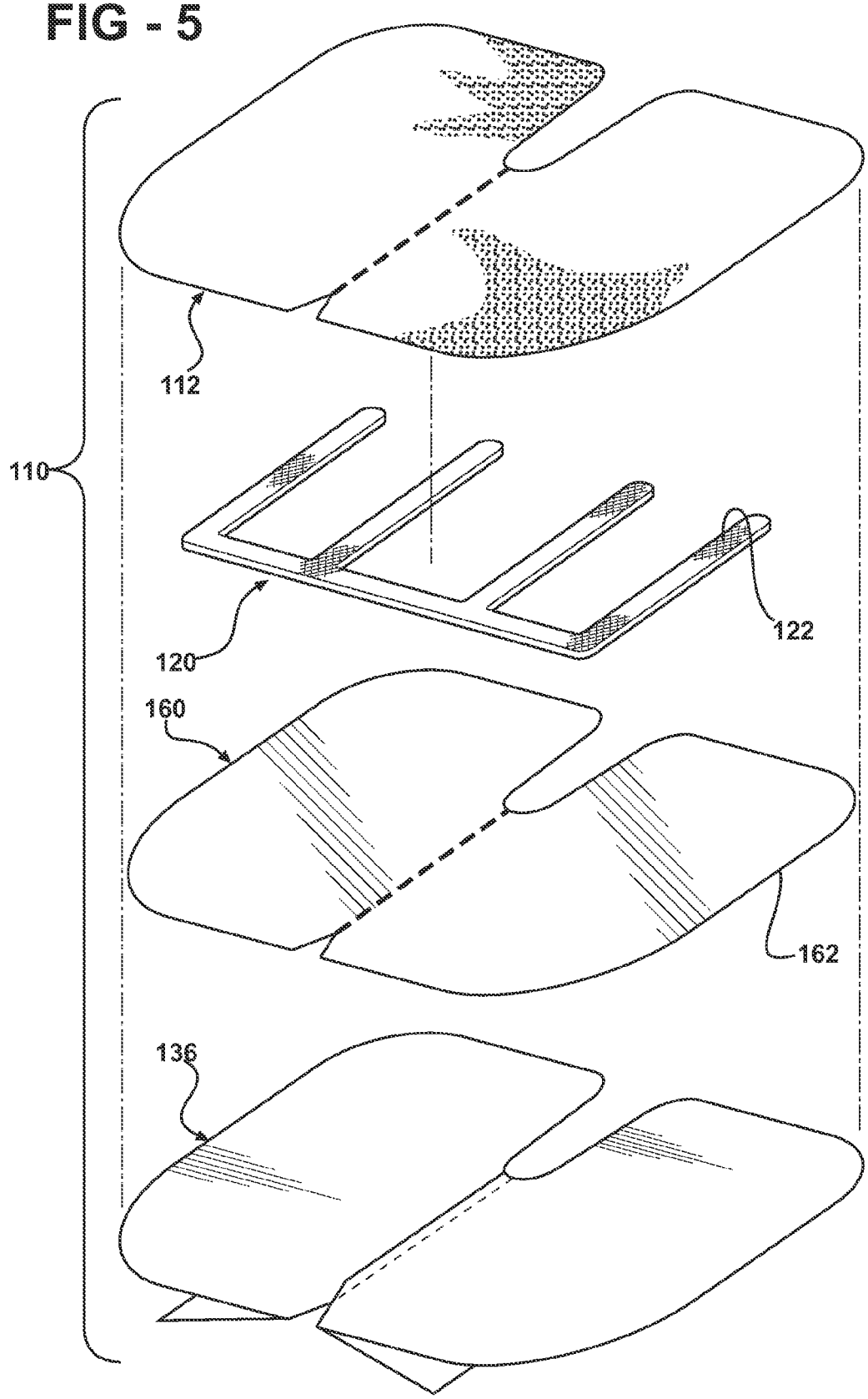
FIG. 5 is an exploded view of a reinforced closure anchor in accordance with the invention.

In an alternative embodiment, the reinforced closure anchor may further include a film layer such as a polyurethane film or similar. As shown in FIG. 5, the reinforced closure anchor 110 includes a fabric layer 112 and an anchor member layer 120 including a reinforcing structure 122 disposed on and adhered to a side of the fabric layer 112. The fabric layer 112 and anchor member layer 120 may have any of the features described in the first embodiment. The reinforced closure anchor 110 further includes a film layer 160 having an adhesive skin-adhering side 162. The adhesive on the skin-adhering side 162 may be a medical skin contact grade adhesive or similarly suitable adhesive. A side of the film layer 160 opposite the skin-adhering side 162 is disposed adjacent the anchor member 120 and is adhered to the anchor member. The film layer 160 may also be adhered to portions of the fabric layer 112 that are not overlapped by the anchor member 120. A release liner 136 may be releasably mounted on the skin-adhering side 162 of the film layer 160. The film layer 160 may have a shape that is coincident with the fabric layer 112. The film layer 160 may make the reinforced closure anchor 110 more comfortable for a patient by shielding the anchor member 120 from the patient's skin, such as in a case where the anchor member is prickly or otherwise irritating when rubbed against skin. The film layer 160 also can create a bacterial barrier and can add stack strength to the closure anchor.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A reinforced closure anchor comprising:
   a fabric layer having an adhesive side, an opposite non-adhesive side, and an outer edge; and
   an anchor member layer having a reinforcing structure, a first side, and an opposite non-adhesive second side, said anchor member non-adhesive second side being adhered to said fabric layer adhesive side; said anchor member being disposed within the outer edge of said fabric layer, and said anchor member being one of a spine and rib shape and a narrow fingers shape.

2. The reinforced closure anchor of claim 1, including a film layer having an adhesive skin-adhering side and an opposite side disposed adjacent said anchor member.

3. The reinforced closure anchor of claim 1, wherein said anchor member first side has an adhesive thereon.

4. The reinforced closure anchor of claim 1, wherein said anchor member is smaller in surface area than said fabric layer.

5. The reinforced closure anchor of claim 4, wherein said anchor member has less than half the surface area of said fabric layer.

6. The reinforced closure anchor of claim 1, wherein said anchor member covers only a portion of said fabric layer adhesive side.

7. The reinforced closure anchor of claim 1, wherein said reinforced closure anchor is generally symmetrical about one of its axes.

8. The reinforced closure anchor of claim 1, including a perforation line extending across said fabric layer and said anchor member.

9. The reinforced closure anchor of claim 8, wherein said reinforced closure anchor is generally symmetrical about one axis, and said perforation line extends along said axis.

10. The reinforced closure anchor of claim 9, including a V-shaped notch along the outer edge of said fabric layer at an end of said perforation line.

11. The reinforced closure anchor of claim 1, including a U-shaped recess along the outer edge of said fabric layer.

12. The reinforced closure anchor of claim 1, including a release liner releasably mounted on the adhesive side of said fabric layer.

13. The reinforced closure anchor of claim 12, wherein said release liner includes a first member and a second member, each of the first member and second member including a first portion mounted on said adhesive side of said fabric layer and a second portion folded relative to said first portion to form a gripping tab;
 wherein one of said first and second members overlaps the other of said first and second members, and one of said first and second members is releasable from said adhesive side of said fabric layer without tampering with the other of said members.

* * * * *